United States Patent
Tsubokura et al.

(10) Patent No.: US 9,242,862 B2
(45) Date of Patent: Jan. 26, 2016

(54) PROCESS FOR PRODUCTION OF FLUOROSULFONYLIMIDE AMMONIUM SALT

(75) Inventors: Shiro Tsubokura, Takaoka (JP); Michiaki Maruyama, Myoko (JP)

(73) Assignee: Nippon Soda Co., Ltd., Tokyo (JP)

( * ) Notice: Subject to any disclaimer, the term of this patent is extended or adjusted under 35 U.S.C. 154(b) by 178 days.

(21) Appl. No.: 13/984,069

(22) PCT Filed: Jan. 30, 2012

(86) PCT No.: PCT/JP2012/051952
§ 371 (c)(1),
(2), (4) Date: Aug. 7, 2013

(87) PCT Pub. No.: WO2012/108284
PCT Pub. Date: Aug. 16, 2012

(65) Prior Publication Data
US 2013/0323154 A1 Dec. 5, 2013

(30) Foreign Application Priority Data
Feb. 10, 2011 (JP) .................................. 2011-027563

(51) Int. Cl.
| | |
|---|---|
| C01B 21/086 | (2006.01) |
| C07C 209/00 | (2006.01) |
| C01B 21/092 | (2006.01) |
| C01B 21/093 | (2006.01) |
| C07C 303/40 | (2006.01) |
| H01M 8/10 | (2006.01) |
| H01M 10/0568 | (2010.01) |

(52) U.S. Cl.
CPC ............ *C01B 21/086* (2013.01); *C01B 21/092* (2013.01); *C01B 21/093* (2013.01); *C07C 209/00* (2013.01); *C07C 303/40* (2013.01); *H01M 8/1048* (2013.01); *H01M 10/0568* (2013.01)

(58) Field of Classification Search
CPC .. C01B 21/086; C01B 21/092; C01B 21/093; C07C 209/00; C07C 303/40
See application file for complete search history.

(56) References Cited

U.S. PATENT DOCUMENTS

| | | | |
|---|---|---|---|
| 4,374,818 | A | 2/1983 | Rieck |
| 5,916,475 | A | 6/1999 | Michot et al. |
| 6,107,493 | A | 8/2000 | Pohl et al. |
| 6,365,301 | B1 | 4/2002 | Michot et al. |
| 2009/0292105 | A1 | 11/2009 | Michot |
| 2010/0137609 | A1 | 6/2010 | Iwaya |
| 2013/0323155 | A1 | 12/2013 | Tsubokura et al. |

FOREIGN PATENT DOCUMENTS

| | | |
|---|---|---|
| CN | 1469845 A | 1/2004 |
| CN | 101503382 A | 1/2004 |
| CN | 101778835 A | 7/2010 |
| EP | 2476666 A1 | 7/2012 |
| JP | 57-95813 A | 6/1982 |
| JP | 08-511274 A | 11/1996 |
| JP | 2000-506132 A | 5/2000 |
| JP | 2001-527505 A | 12/2001 |
| JP | 2010-168249 A | 8/2010 |
| JP | 2010-168308 A | 8/2010 |
| JP | 2010-189372 A | 9/2010 |
| WO | WO 97/31909 A1 | 9/1997 |
| WO | WO 2009/123328 A1 | 10/2009 |
| WO | WO 2010/010613 A1 | 1/2010 |

OTHER PUBLICATIONS

Appel et al., "About the reaction of sulfuryl diisocyanate with halogenosulfuric acid. A simple method for producing fluorosulfonyl isocyanate and bis(fluorosulfonyl)imide," Chemische Berichte, 1964, 97:849-850, with English translation.
Beran et al., "A New Method of the Preparation of Imido-bis(sulfuric acid) Dihalogenide, (F,Ci), and the Potassium Salt of Imido-bis-(sulfuric acid) Difluoride," Z. Anorg. Allg. Chem., 2005, 631:55-59.
Krumm et al., "Synthesis of Poly- and the First Perfluoroalkyl-$N(SO_2F)_2$Derivatives: Improved Methods for the Preparation of $XN(SO_2F)_2(X = H, Cl)$ and Single-Crystal Diffraction Stufies of $HN(SO_2Cl)_2$, $HN(SO_2F)_2$ and $CF_3CH_2N(SO_2F)_2$," Inorg. Chem., 1998, 37(24):6295-6303.
Paul et al., "Chemistry of Imidobis(Sulphuryl Chloride)-III, Solvolytic Reactions and the Nature of the Solvolysed Products," J. Inorg. Nucl. Chem., 1978, 40:2001-2003.
Ruff et al., "Imidodisulfuryl fluoride, cesium imidodisulfuryl fluoride, and fluoroimidodisulfuryl fluoride," Inorg. Synth., 1968, 11:138-140.
Růžička et al., "For Synthesis of Ammonium Bis(fluorosulfonylimide) $NH_4(SO_2F)_2$," Zeitschrift fuer Chemie, 1987, 27(6):227-228, with English translation.
Vacuubrand http://www.vacuubrand.com/us/page823.html, downloaded May 28, 2015, one page.
International Search Report dated Mar. 27, 2012, in PCT/JP2012/054888.
Office Action dated Feb. 20, 2014, in TW 101106685, with partial English translation of search report.
Office Action dated Jul. 31, 2014, in CN 201280010507.4, with partial English translation of search report.
Office Action dated Aug. 29, 2014, in U.S. Appl. No. 13/985,915.
Search Report dated Nov. 18, 2014, in EP 12752499.9.
Final Office Action dated Mar. 6, 2015, in U.S. Appl. No. 13/985,915.
Office Action dated Jun. 4, 2015, in U.S. Appl. No. 13/985,915.

*Primary Examiner* — Paul A Zucker
*Assistant Examiner* — Mark Luderer
(74) *Attorney, Agent, or Firm* — Foley & Lardner LLP

(57) ABSTRACT

A compound [I] such as ammonium N-(chlorosulfonyl)-N-(fluorosulfonyl)imide is reacted with hydrogen fluoride to obtain a compound [II] such as ammonium N,N-di(fluorosulfonyl)imide. The obtained compound [II] is reacted with an alkali metal compound or the like to obtain a compound [IV] such as an N,N-di(fluorosulfonyl)imide alkali metal salt.

4 Claims, No Drawings

PROCESS FOR PRODUCTION OF FLUOROSULFONYLIMIDE AMMONIUM SALT

CROSS-REFERENCE TO RELATED APPLICATIONS

This application is a National Stage application of PCT/JP2012/051952, filed Jan. 30, 2012, which claims priority from Japanese application JP2011-027563, filed Feb. 10, 2011.

TECHNICAL FIELD

The present invention relates to a process for producing a fluorosulfonylimide ammonium salt. More specifically, the present invention relates to a process for producing a fluorosulfonylimide ammonium salt with good efficiency and maximum suppression of the contamination of metal impurities that degrade electrolyte properties and the like.

Priority is claimed on Japanese Patent Application No. 2011-027563, filed Feb. 10, 2011, the content of which is incorporated herein by reference.

BACKGROUND ART

Fluorosulfonylimide salts are useful compounds in a wide variety of fields, and are used as electrolytes, as additives added to the electrolytes of fuel cells, and as selective electron withdrawing compounds and the like (see Patent Document 1). Fluorosulfonylimide alkali metal salts and various fluorosulfonylimide onium salts can be obtained by reactions using an alkali metal compound or an onium compound. Fluorosulfonylimide ammonium salts are useful as production intermediates for fluorosulfonylimide alkali metal salts and fluorosulfonylimide onium salts other than the ammonium salts.

Various processes have been proposed for synthesizing fluorosulfonylimide ammonium salts. For example, Non-Patent Document 1 discloses a process of synthesizing a di(fluorosulfonyl)imide ammonium salt from di(fluorosulfonyl)imide and ammonia.

Patent Document 2 discloses a process for synthesizing a bis[di(fluorosulfonyl)imide]onium salt by reacting di(chlorosulfonyl)imide with an onium compound to obtain a chlorosulfonylimide onium salt, and then reacting this onium salt with a fluoride containing at least one element selected from the group consisting of elements of group 11 to group 15 in the fourth period to sixth period (but excluding arsenic and antimony). Examples of the fluoride available in the production process described in Patent Document 2 include zinc fluoride ($ZnF_2$), copper fluoride ($CuF_2$) and bismuth fluoride ($BiF_2$). These compounds are all solid substances at normal temperature.

Further, Non-Patent Documents 2 and 3 disclose a process for directly synthesizing di(fluorosulfonyl)imides from di(chlorosulfonyl)imides using arsenic trifluoride ($AsF_3$) or antimony trifluoride ($SbF_3$) as a fluorinating agent.

DOCUMENTS OF RELATED ART

Patent Documents

Patent Document 1: Published Japanese Translation No. Hei 08-511274 of PCT
Patent Document 2: Japanese Unexamined Patent Application, First Publication No. 2010-168308

Non-Patent Documents

Non-Patent Document 1: Zeitschrift fuer Chemie (1987), 27(6), 227-8
Non-Patent Document 2: John K. Ruff and Max Lustig, Inorg. Synth., 11, 138 to 140 (1968)
Non-Patent Document 3: Jean'ne M. Shreeve et al. Inorg. Chem., 1998, 37(24), 6295 to 6303

DISCLOSURE OF INVENTION

Problems to be Solved by the Invention

The di(fluorosulfonyl)imide available as a starting material in the synthetic process disclosed in Non-Patent Document 1 can be obtained by treating and freeing a di(fluorosulfonyl)imide salt with a strong acid. However, because di(fluorosulfonyl)imide is itself a strong acid, industrial production thereof is not easy. Although there is a process for synthesizing di(fluorosulfonyl)imide using an ion exchange resin, steps thereof are complex, and the process is not suitable for industrial production.

In the synthetic process disclosed in Patent Document 2, because the metal element derived from the fluoride causes a deterioration in the electrolyte properties, the metal element derived from the fluoride must be removed. In order to completely remove the metal element, a complex refining operation must be performed.

The $AsF_3$ available in the synthetic process disclosed in Non-Patent Document 2 or 3 is comparatively expensive. Both As and Sb are elements that exhibit a high level of toxicity, and therefore workability is problematic. Particularly in the case of the synthetic process using $AsF_3$, compounds that are difficult to be separated from the target product are produced as by-products. As a result, the synthetic process disclosed in Non-Patent Documents 2 or 3 is unsuitable for industrial production.

An object of the present invention is to provide a process for producing a fluorosulfonylimide ammonium salt with good efficiency and maximum suppression of the contamination of metal impurities that degrade electrolyte properties and the like, and also to provide a process for producing a fluorosulfonylimide salt containing no metal impurities that degrade electrolyte properties and the like from the fluorosulfonylimide ammonium salt.

Means to Solve the Problems

The inventors of the present invention undertook intensive investigations in order to achieve the above object. As a result they discovered that by reacting a specific chlorosulfonylimide ammonium salt with hydrogen fluoride, a fluorosulfonylimide ammonium salt could be synthesized in an industrially simple manner. Further, they also discovered that by reacting the thus obtained fluorosulfonylimide ammonium salt with an alkali metal compound or the like, a fluorosulfonylimide alkali metal salt or the like containing no metal impurities that degrade electrolyte properties and the like could be obtained. The present invention was completed on the basis of these findings.

In other words, the present invention includes the following aspects.
(1) A process for producing a fluorosulfonylimide ammonium salt represented by formula [II] (hereafter also referred to as "compound [II]"), the process including reacting a compound represented by formula [I] (hereafter also referred to as "compound [I]") and hydrogen fluoride.

(2) The process disclosed above in (1), further including reacting a compound represented by formula [III] (hereafter also referred to as "compound [III]") with ammonia or a salt thereof to obtain the compound represented by formula [I].
(3) A process for producing a fluorosulfonylimide salt represented by formula [IV] (hereafter also referred to as "compound [IV]"), the process including reacting the fluorosulfonylimide ammonium salt represented by formula [II] obtained by the process disclosed above in (1) or (2) with at least one compound selected from the group consisting of alkali metal compounds, onium compounds and organic amine compounds.

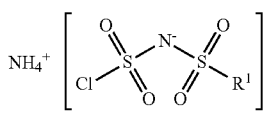

In formula [I], $R^1$ represents a fluorine atom, a chlorine atom, or a fluoroalkyl group having 1 to 6 carbon atoms.

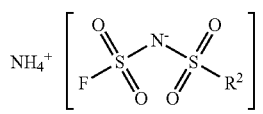

In formula [II], $R^2$ represents a fluorine atom or a fluoroalkyl group having 1 to 6 carbon atoms.

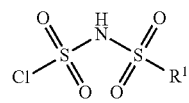

In formula [III], $R^1$ is the same as defined above in formula [I].

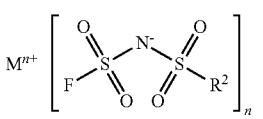

In formula [IV], $M^{n+}$ represents an alkali metal cation or an onium cation (excluding $NH_4^+$), n corresponds with the valency of the alkali metal cation or onium cation (excluding $NH_4^+$) and is an integer of 1 to 3, and $R^2$ is the same as defined above in formula [II].
(4) The process disclosed above in (3), wherein the compound reacted with the fluorosulfonylimide ammonium salt represented by formula [II] is an alkali metal hydroxide or a tertiary amine compound, and $M^{n+}$ in formula [IV] represents an alkali metal cation or a tertiary ammonium cation.

Effects of the Invention

The present invention enables a fluorosulfonylimide ammonium salt to be produced in an industrially efficient manner. Further, by reacting the thus obtained fluorosulfonylimide ammonium salt with an alkali metal compound or the like, another fluorosulfonylimide salt containing no metal impurities that degrade electrolyte properties and the like can be produced.

EMBODIMENTS OF THE INVENTION

In the following description, unless specifically stated otherwise, the term "fluorosulfonylimide" refers to di(fluorosulfonyl)imide having two fluorosulfonyl groups and N-(fluorosulfonyl)-N-(fluoroalkylsulfonyl)imides having a fluorosulfonyl group and a fluoroalkylsulfonyl group. Further, the term "chlorosulfonylimide" is similarly defined. The aforementioned term "fluoroalkyl" describes an alkyl group of 1 to 6 carbon atoms in which at least one hydrogen atom has been substituted with a fluorine atom, and examples thereof include a fluoromethyl group, difluoromethyl group, trifluoromethyl group, fluoroethyl group, difluoroethyl group, trifluoroethyl group, and pentafluoroethyl group.
(Process for Producing Compound [II])
The process for producing a compound [II] according to the present invention includes a step of reacting a compound [I] and hydrogen fluoride.
The compound [I] available in the present invention is a compound represented by formula [I].

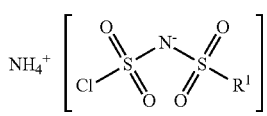

In formula [I], $R^1$ represents a fluorine atom, a chlorine atom, or a fluoroalkyl group having 1 to 6 carbon atoms. Of these, $R^1$ is preferably a chlorine atom.
The number of carbon atoms constituting the fluoroalkyl group for $R^1$ is from 1 to 6, preferably from 1 to 4, and more preferably from 1 to 2. Examples of the fluoroalkyl group include a fluoromethyl group, difluoromethyl group, trifluoromethyl group, fluoroethyl group, difluoroethyl group, 2,2,2-trifluoroethyl group, pentafluoroethyl group, 3,3,3-trifluoropropyl group, perfluoro-n-propyl group, fluoropropyl group, perfluoroisopropyl group, fluorobutyl group, 3,3,4,4,4-pentafluorobutyl group, perfluoro-n-butyl group, perfluoroisobutyl group, perfluoro-t-butyl group, perfluoro-sec-butyl group, fluoropentyl group, perfluoropentyl group, perfluoroisopentyl group, perfluoro-t-pentyl group, fluorohexyl group, perfluoro-n-hexyl group and perfluoroisohexyl group. Among these groups, a trifluoromethyl group, pentafluoroethyl group or perfluoro-n-propyl group is preferable, and a trifluoromethyl group or pentafluoroethyl group is more preferable.
Specific examples of the compound [I] include ammonium N-(chlorosulfonyl)-N-(fluorosulfonyl)imide, ammonium di(chlorosulfonyl)imide, ammonium N-(chlorosulfonyl)-N-(trifluoromethylsulfonyl)imide, ammonium N-(chlorosulfonyl)-N-(pentafluoroethylsulfonyl)imide, and ammonium N-(chlorosulfonyl)-N-(perfluoro-n-propylsulfonyl)imide.
There are no particular limitations on the process used for producing the compound [I]. One preferred process for producing the compound [I] is a process that includes reacting a compound [III] with ammonia or a salt thereof.
Examples of ammonia salts available in the synthesis reaction for the compound [I] include ammonium halides such as ammonium chloride, ammonium bromide and ammonium iodide.

The compound [III] is a compound represented by formula [III].

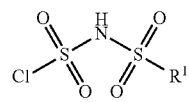

In formula [III], $R^1$ is the same as defined above in formula [I].

Specific examples of the compound [III] include N-(chlorosulfonyl)-N-(fluorosulfonyl)imide, di(chlorosulfonyl) imide, N-(chlorosulfonyl)-N-(trifluoromethylsulfonyl) imide, N-(chlorosulfonyl)-N-(pentafluoroethylsulfonyl) imide, and N-(chlorosulfonyl)-N-(perfluoro-n-propylsulfonyl)imide.

The compound [III] may be a commercially available material, or may be synthesized, for example, using the process disclosed in Z. Anorg. Allg. Chem., 2005, 631, 55 to 59. For example, di(chlorosulfonyl)imide, which is one compound represented by formula [III], can be obtained by reacting chlorosulfonyl isocyanate and chlorosulfonic acid (see Chemisch Berichte 1964, 97, 849 to 850).

Further, N-(chlorosulfonyl)-N-(fluoroalkylsulfonyl)imides can be obtained by a reaction between chlorosulfonyl isocyanate and a fluoroalkylsulfonic acid, or by a reaction between a fluoroalkylsulfonyl isocyanate and chlorosulfonic acid.

The reaction between the compound [III] and ammonia or a salt thereof can be performed by mixing the reactants, either within a solvent or in the absence of a solvent (for example, see J. Inorg. Nucl. Chem., 1978, 40, 2001 to 2003). The reaction temperature is preferably within a range from −40° C. to 200° C., and more preferably from −20° C. to 100° C. The reaction time varies depending on the reaction scale, but is preferably from 0.1 hours to 48 hours, and more preferably from 0.5 hours to 24 hours.

In the reaction between the compound [III] and ammonia or a salt thereof, the amount used of the ammonia or salt thereof is preferably within a range from 1 mol to 5 mol, and more preferably from 1 mol to 2 mol, relative to 1 mol of the compound [III].

Examples of the solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyl oxazolidinone, valeronitrile, benzonitrile, acetonitrile, ethyl acetate, isopropyl acetate, butyl acetate, nitromethane, nitrobenzene, toluene, chlorobenzene, methylene chloride, carbon tetrachloride and chloroform. From the viewpoint of achieving superior workability during refining, a low-boiling point solvent is preferable. Examples of solvents having this type of preferred property include acetonitrile, ethyl acetate, isopropyl acetate, butyl acetate, methylene chloride, carbon tetrachloride and chloroform.

Following completion of the synthesis reaction described above, the obtained compound [I] may be used in the process for producing the compound [II] according to the present invention without any further refining, or may be subjected to post-processing and refining using normal methods before being used in the process for producing the compound [II] according to the present invention.

The hydrogen fluoride available in the present invention is the compound represented by the molecular formula HF. Hydrogen fluoride is a colorless gas or liquid, and can therefore be easily transported into the reaction apparatus via a pipe or the like.

Hydrogen fluoride can be produced by mixing and heating fluorite (a mineral ore containing calcium fluoride $CaF_2$ as the main component) and concentrated sulfuric acid. Further, hydrogen fluoride can also be obtained by reacting fluorine $F_2$ with water.

The amount of hydrogen fluoride used is preferably within a range from 1 mol to 20 mol, more preferably from 1 mol to 10 mol, and still more preferably from 1 mol to 5 mol, relative to 1 mol of the compound [I].

The reaction between the compound [I] and hydrogen fluoride can be conducted within an organic solvent or in the absence of a solvent. There are no particular limitations on the organic solvents available in the reaction, provided they do not impair the fluorination reaction. Examples of the solvent include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyl oxazolidinone, acetonitrile, valeronitrile, benzonitrile, ethyl acetate, isopropyl acetate, butyl acetate, nitromethane, nitrobenzene, toluene, chlorobenzene, methylene chloride, carbon tetrachloride and chloroform. From the viewpoint of achieving smooth progression of the fluorination reaction, the use of a polar solvent is preferable. Examples of preferred solvents include acetonitrile, ethyl acetate, isopropyl acetate and butyl acetate.

The organic solvent is preferably dewatered prior to use. If water exists, then the di(chlorosulfonyl)imide or di(chlorosulfonyl)imide ammonium salt becomes more prone to decomposition, and therefore there is a possibility that the yield may deteriorate.

The temperature of the fluorination reaction may be adjusted appropriately in accordance with the state of progression of the reaction, but is preferably within a range from −40° C. to 200° C., and more preferably from −20° C. to 100° C. The time required for the reaction varies depending on the reaction scale, but is preferably from 0.1 hours to 48 hours, and more preferably from 0.5 hours to 24 hours.

The compound [II] can be obtained by the production process according to the present invention.

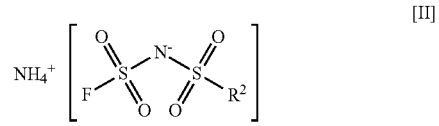

In formula [II], $R^2$ represents a fluorine atom or a fluoroalkyl group having 1 to 6 carbon atoms. Examples of the fluoroalkyl group include the same groups as those mentioned above within the description of $R^1$.

Specific examples of the compound represented by formula [II] include ammonium di(fluorosulfonyl)imide, ammonium N-(fluorosulfonyl)-N-(trifluoromethylsulfonyl)

imide, ammonium N-(fluorosulfonyl)-N-(pentafluoroethyl-sulfonyl)imide, and ammonium N-(fluorosulfonyl)-N-(per-fluoro-n-propylsulfonyl)imide. Among these, ammonium di(fluorosulfonyl)imide is preferable.

The compound [II] is useful as an intermediate for producing a fluorosulfonylimide salt represented by formula [IV]. Further, the compound [II] obtained in the manner described above is also useful as a material for an ion conductor used in forming primary cells, secondary cells such as a lithium (ion) secondary cell, and electrochemical devices such as electrolytic capacitors, electrical double-layer capacitors, fuel cells, solar cells and electrochromic elements.

(Process for Producing Compound [IV])

The process for producing a compound [IV] according to the present invention includes a step of reacting the compound [II] obtained using the production process described above with at least one compound selected from the group consisting of alkali metal compounds, onium compounds and organic amine compounds.

This reaction may be performed by mixing, in the presence of a solvent, the compound [II] and at least one compound selected from the group consisting of alkali metal compounds, onium compounds and organic amine compounds.

Examples of the alkali metal compounds available in the reaction include hydroxides such as LiOH, NaOH, KOH, RbOH and CsOH, carbonates such as $Li_2CO_3$, $Na_2CO_3$, $K_2CO_3$, $Rb_2CO_3$ and $Cs_2CO_3$, hydrogen carbonates such as $LiHCO_3$, $NaHCO_3$, $KHCO_3$, $RbHCO_3$ and $CsHCO_3$, chlorides such as LiCl, NaCl, KCl, RbCl and CsCl, bromides such as LiBr, NaBr, KBr, RbBr and CsBr, fluorides such as LiF, NaF, KF, RbF and CsF, alkoxide compounds such as $CH_3OLi$, EtOLi, t-BuOK and t-BuONa, hydrides such as NaH, KH and LiH, and alkyllithium compounds such as i-$Pr_2NLi$, EtLi, BuLi and t-BuLi (wherein Et represents an ethyl group, Pr represents a propyl group and Bu represents a butyl group). Of these compounds, a hydroxide is preferable. By using a hydroxide, ammonia is produced as a by-product of the reaction, and therefore by removing this ammonia under reduced pressure, the equilibrium can be adjusted to a state that promotes the reaction. By using an alkali metal compound, inorganic salt by-products can be removed by filtration and water washing, meaning the product can be easily purified.

The amount of the alkali metal compound used is preferably from 1 mol to 10 mol, and more preferably from 1 mol to 5 mol, relative to 1 mol of the compound [II].

Examples of the onium compounds available in the reaction include nitrogen-based onium compounds such as imidazolium compounds, pyrazolium compounds, pyridinium compounds, pyrrolidinium compounds, piperidinium compounds, morpholinium compounds and quaternary ammonium compounds, phosphorus-based onium compounds such as quaternary phosphonium compounds and tertiary phosphine compounds, sulfur-based onium compounds such as sulfonium compounds, as well as guanidinium compounds, isouronium compounds and isothiouronium compounds. Among these compounds, organic onium compounds such as imidazolium compounds and pyridinium compounds are preferable. Further, the onium compound preferably contains no metal elements that degrade electrolyte properties and the like.

Specific examples of the imidazolium compounds include chlorides such as 1,3-dimethylimidazolium chloride, 1-ethyl-3-methylimidazolium chloride, 1-butyl-3-methylimidazolium chloride, 1-hexyl-3-methylimidazolium chloride, 1-octyl-3-methylimidazolium chloride, 1-allyl-3-ethylimidazolium chloride, 1-allyl-3-butylimidazolium chloride, 1,3-diallylimidazolium chloride, 1-ethyl-2,3-dimethylimidazolium chloride, 1-butyl-2,3-dimethylimidazolium chloride and 1-hexyl-2,3-dimethylimidazolium chloride; bromides such as 1,3-dimethylimidazolium bromide, 1-ethyl-3-methylimidazolium bromide, 1-butyl-3-methylimidazolium bromide, 1-hexyl-3-methylimidazolium bromide, 1-octyl-3-methylimidazolium bromide, 1-allyl-3-ethylimidazolium bromide, 1-allyl-3-butylimidazolium bromide, 1,3-diallylimidazolium bromide, 1-ethyl-2,3-dimethylimidazolium bromide, 1-butyl-2,3-dimethylimidazolium bromide and 1-hexyl-2,3-dimethylimidazolium bromide;

iodides such as 1,3-dimethylimidazolium iodide, 1-ethyl-3-methylimidazolium iodide, 1-butyl-3-methylimidazolium iodide, 1-hexyl-3-methylimidazolium iodide, 1-octyl-3-methylimidazolium iodide, 1-allyl-3-ethylimidazolium iodide, 1-allyl-3-butylimidazolium iodide, 1,3-diallylimidazolium iodide, 1-ethyl-2,3-dimethylimidazolium iodide, 1-butyl-2,3-dimethylimidazolium iodide and 1-hexyl-2,3-dimethylimidazolium iodide; and hydroxides such as 1,3-dimethylimidazolium hydroxide, 1-ethyl-3-methylimidazolium hydroxide, 1-butyl-3-methylimidazolium hydroxide, 1-hexyl-3-methylimidazolium hydroxide, 1-octyl-3-methylimidazolium hydroxide, 1-allyl-3-ethylimidazolium hydroxide, 1-allyl-3-butylimidazolium hydroxide, 1,3-diallylimidazolium hydroxide, 1-ethyl-2,3-dimethylimidazolium hydroxide, 1-butyl-2,3-dimethylimidazolium hydroxide and 1-hexyl-2,3-dimethylimidazolium hydroxide.

Specific examples of the pyrazolium compounds include chlorides such as 2-ethyl-1,3,5-trimethylpyrazolium chloride, 2-propyl-1,3,5-trimethylpyrazolium chloride, 2-butyl-1,3,5-trimethylpyrazolium chloride and 2-hexyl-1,3,5-trimethylpyrazolium chloride; bromides such as 2-ethyl-1,3,5-trimethylpyrazolium bromide, 2-propyl-1,3,5-trimethylpyrazolium bromide, 2-butyl-1,3,5-trimethylpyrazolium bromide and 2-hexyl-1,3,5-trimethylpyrazolium bromide; and hydroxides such as 2-ethyl-1,3,5-trimethylpyrazolium hydroxide, 2-propyl-1,3,5-trimethylpyrazolium hydroxide, 2-butyl-1,3,5-trimethylpyrazolium hydroxide and 2-hexyl-1,3,5-trimethylpyrazolium hydroxide.

Specific examples of the pyridinium compounds include 1-acetonylpyridinium chloride, 1-aminopyridinium iodide, 2-benzyloxy-1-methylpyridinium trifluoromethanesulfonate, 1,1'-[biphenyl-4,4'-diylbis(methylene)]-bis(4,4'-bipyridinium)bis(hexafluorophosphate), 1,1'-[biphenyl-4,4'-diylbis(methylene)]-bis(4,4'-bipyridinium)dibromide, 1,1'-bis(2,4-dinitrophenyl)-4,4'-bipyridinium dichloride, bis(2,4,6-trimethylpyridine)bromonium hexafluorophosphate, 2-bromo-1-ethylpyridinium tetrafluoroborate, 4-bromopyridine hydrobromide, 4-bromopyridine hydrochloride, 1-butyl-4-methylpyridinium bromide, 1-butyl-3-methylpyridinium bromide, 1-butyl-3-methylpyridinium chloride, 1-butyl-4-methylpyridinium chloride, 1-butyl-4-methylpyridinium hexafluorophosphate, 1-butylpyridinium bromide, 1-butylpyridinium chloride, 1-butylpyridinium hexafluorophosphate, 1-butylpyridinium tetrafluoroborate, 4-carbamoyl-1-hexadecylpyridinium chloride, 1-(carbamoylmethyl)pyridinium chloride, 3-carbamoyl-1-methylpyridibium chloride, 4-picolyl chloride hydrochloride, 2-(chloromethyl) pyridine hydrochloride, 3-(chloromethyl)pyridine hydrochloride, 2-chloro-1-methylpyridinium iodide, 2-chloro-1-methylpyridinium p-toluenesulfonate, 4-chloropyridine hydrochloride, cetylpyridinium chloride, 1-cyano-4-(dimethylamino)pyridinium tetrafluoroborate, 1-(cyanomethyl)pyridinium chloride, cyclobis(paraquat-1,4-phenylene)tetrakis(hexafluorophosphate), 1,1'-dibenzyl-4,4'- bipyridinium dichloride hydrate, 2,6-dichloro-1-fluoropyridinium trifluoromethanesulfonate, 1,1'-difluoro-2,2'-bipyridinium bis(tetrafluoroborate), 1,1'-diheptyl-4,4'-bipyridinium dibromide, 2,6-pyridinediol hydrochloride, 4-dimethylamino-1-neopentylpyridinium chloride, 4-dimethylaminopyridinium bromide perbromide, 4-(dimethylamino)-1-(triphenylmethyl)pyridinium chloride, 1,1'-dimethyl-4,4'-bipyridinium dichloride hydrate, 1,1'-dimethyl-4,4'-bipyridinium dichloride, 1-(dimethylcarbamoyl)-4-(2-sulfoethyl)pyridinium hydroxide intramolecular salt, 2,6-dimethylpyridinium p-toluenesulfonate, 1,1'-di-n-octyl-4,4'-bipyridinium dibromide, 1,1'-diphenyl-4,4'-bipyridinium dichloride, 1-dodecylpyridinium chloride, 1-ethyl-3-(hydroxymethyl)pyridinium ethyl sulfate, 1-ethyl-4-(methoxycarbonyl)pyridinium iodide, 1-ethyl-3-methylpyridinium bis(trifluoromethanesulfonyl)imide, 1-ethyl-3-methylpyridinium ethyl sulfate, 1-ethylpyridinium bromide, 1-ethylpyridinium chloride, 1-fluoro-2,6-dichloropyridinium tetrafluoroborate, 2-fluoro-1-methylpyridinium p-toluenesulfonate, 1-fluoropyridinium pyridine heptafluorodiborate, 1-fluoropyridinium tetrafluoroborate, 1-fluoropyridinium trifluoromethanesulfonate, 1-fluoro-2,4,6-trimethylpyridinium tetrafluoroborate, 1-fluoro-2,4,6-trimethylpyridinium trifluoromethanesulfonate, Girard's reagent P, 1-hexadecyl-4-methylpyridinium chloride hydrate, hexadecylpyridinium bromide hydrate, hexadecylpyridinium chloride monohydrate, isonicotinoyl chloride hydrochloride, MDEPAP, 1-methylpyridinium-2-aldoxime chloride, 1-methylpyridinium chloride, NDEPAP, 1-octadecyl-4-(4-phenyl-1,3-butadienyl)pyridinium bromide, N-octadecyl-4-stilbazole bromide, 1-(10,12-pentacosadiynyl)pyridinium bromide, 1-phenacylpyridinium bromide, 1,1'-[1,4-phenylenebis(methylene)]bis(4,4'-bipyridinium)bis(hexafluorophosphate), 1,1'-[1,4-phenylenebis(methylene)]bis(4,4'-bipyridinium)dibromide, N-phenylnicotinamide hydrochloride, 1-propylpyridinium chloride, pyridine-2-carbonyl chloride hydrochloride, pyridine-2-carboxylic acid hydrochloride, pyridine hydrobromide, pyridine hydrochloride, pyridinium bromide perbromide, pyridinium chlorochromate, pyridinium dichromate, pyridinium fluorochromate, pyridinium 3-nitrobenzenesulfonate, pyridinium poly(hydrogen fluoride), pyridinium p-toluenesulfonate, pyridinium trifluoromethanesulfonate, pyridostigmine bromide, pyridoxamine dihydrochloride monohydrate, pyridoxine hydrochloride, 3-pyridylacetic acid hydrochloride, 2-pyridylacetic acid hydrochloride, 1-(4-pyridyl)pyridinium chloride hydrochloride hydrate, 1-(3-sulfopropyl)pyridinium hydroxide intramolecular salt, α,β,γ,δ-tetrakis(1-methylpyridinium-4-yl)porphyrin p-toluenesulfonate, 1-(trifluoroacetyl)-4-(dimethylamino) pyridinium trifluoroacetate, 1-methylpyridinium-3-carboxylic acid hydrochloride, and 2,4,6-trimethylpyridinium p-toluenesulfonate.

Specific examples of the pyrrolidinium compounds include 1-butyl-1-methylpyrrolidinium bromide, 1-butyl-1-methylpyrrolidinium chloride, 1-butyl-1-propylpyrrolidinium bromide and 1-butyl-1-propylpyrrolidinium chloride.

A specific example of the piperidinium compounds is 1-butyl-1-methylpiperidinium bromide.

Specific examples of the morpholinium compounds include 4-propyl-4-methylmorpholinium chloride, 4-(2-methoxyethyl)-4-methylmorpholinium chloride, 4-propyl-4-methylmorpholinium bromide, 4-(2-methoxyethyl)-4-methylmorpholinium bromide, 4-propyl-4-methylmorpholinium hydroxide, and 4-(2-methoxyethyl)-4-methylmorpholinium hydroxide.

Specific examples of the quaternary ammonium compounds include propyltrimethylammonium chloride, fluorides such as diethyl-2-methoxyethylmethylammonium fluoride, methyltrioctylammonium fluoride, cyclohexyltrimethylammonium fluoride and 2-hydroxyethyltrimethylammonium fluoride; chlorides such as propyltrimethylammonium chloride, diethyl-2-methoxyethylmethylammonium chloride, methyltrioctylammonium chloride, cyclohexyltrimethylammonium chloride and 2-hydroxyethyltrimethylammonium chloride; bromides such as propyltrimethylammonium bromide, diethyl-2-methoxyethylmethylammonium bromide, methyltrioctylammonium bromide, cyclohexyltrimethylammonium bromide and 2-hydroxyethyltrimethylammonium bromide; iodides such as propyltrimethylammonium iodide, diethyl-2-methoxyethylmethylammonium iodide, methyltrioctylammonium iodide, cyclohexyltrimethylammonium iodide and 2-hydroxyethyltrimethylammonium iodide; hydroxides such as propyltrimethylammonium hydroxide, diethyl-2-methoxyethylmethylammonium hydroxide, methyltrioctylammonium hydroxide, cyclohexyltrimethylammonium hydroxide and 2-hydroxyethyltrimethylammonium hydroxide; acetates such as propyltrimethylammonium acetate, diethyl-2-methoxyethylmethylammonium acetate, methyltrioctylammonium acetate, cyclohexyltrimethylammonium acetate and 2-hydroxyethyltrimethylammonium acetate; and hydrogen sulfates such as propyltrimethylammonium hydrogen sulfate, diethyl-2-methoxyethylmethylammonium hydrogen sulfate, methyltrioctylammonium hydrogen sulfate, cyclohexyltrimethylammonium hydrogen sulfate and 2-hydroxyethyltrimethylammonium hydrogen sulfate.

Specific examples of the phosphonium compounds include acetonitrilephenylphosphonium chloride, allyltriphenylphosphonium bromide, allyltriphenylphosphonium chloride, amyltriphenylphosphonium bromide, 1H-benzotriazol-1-yloxy-tripyrrolidinophosphonium hexafluorophosphate, 1H-benzotriazol-1-yloxy-tris(dimethylamino)phosphonium hexafluorophosphate, benzyltriphenylphosphonium bromide, benzyltriphenylphosphonium chloride, (bromomethyl)triphenylphosphonium bromide, 3-bromopropyltriphenylphosphonium bromide, trans-2-butene-1,4-bis(triphenylphosphonium chloride), butyltriphenylphosphonium bromide, (4-carboxybutyl)triphenylphosphonium bromide, (3-carboxypropyl) triphenylphosphonium bromide, (4-chlorobenzyl)triphenylphosphonium chloride, (2-chlorobenzyl) triphenylphosphonium chloride, (chloromethyl) triphenylphosphonium chloride, cinnamyltriphenylphosphonium bromide, (cyanomethyl) triphenylphosphonium chloride, cyclopropyltriphenylphosphonium bromide, di-tert-butylmethylphosphonium tetraphenylborate, (2,4-dichlorobenzyl)triphenylphosphonium chloride, 2-dimethylaminoethyltriphenylphosphonium bromide, 2-(1,3-dioxan-2-yl)ethyltriphenylphosphonium bromide, 2-(1,3-dioxolan-2-yl)ethyltriphenylphosphonium bromide, (1,3-dioxolan-2-yl)methyltriphenylphosphonium bromide, 4-ethoxybenzyltriphenylphosphonium bromide, ethoxycarbonylmethyl(triphenyl)phosphonium bromide, ethyltriphenylphosphonium bromide, ethyltriphenylphosphonium iodide, (formylmethyl)triphenylphosphonium chloride, heptyltriphenylphosphonium bromide, hexyltriphenylphosphonium bromide, (2-hydroxybenzyl)triphenylphosphonium bromide, isopropyltriphenylphosphonium iodide, methoxycarbonylmethyl(triphenyl)phosphonium bromide, (methoxymethyl)triphenylphosphonium chloride, (N-methyl-N-phenyl amino)triphenylphosphonium iodide, methyltriphenylphosphonium bromide, methyltriphenylphosphonium iodide, (1-naphthylmethyl)triphenylphosphonium chloride, (4-nitrobenzyl)triphenylphosphonium bromide, μ-oxobis[tris(dimethylamino)phosphonium]bis(tetrafluoroborate), phenacyltriphenylphosphonium bromide, tetrabutylphosphonium benzotriazolate, tetrabutylphosphonium bis(1,3-dithiole-2-thione-4,5-dithiolate)nickel(III) complex, tetrabutylphosphonium bromide, tetrabutylphosphonium chloride, tetrabutylphosphonium hexafluorophosphate, tetrabutylphosphonium hydroxide, tetrabutylphosphonium tetrafluoroborate, tetrabutylphosphonium tetraphenylborate, tetraethylphosphonium bromide, tetraethylphosphonium hexafluorophosphate, tetraethylphosphonium tetrafluoroborate, tetrakis(hydroxymethyl)phosphonium chloride, tetrakis(hydroxymethyl)phosphonium sulfate, tetra-n-octylphosphonium bromide, tetraphenylphosphonium bromide, tetraphenylphosphonium chloride, tetraphenylphosphonium iodide, tetraphenylphosphonium tetraphenylborate, tetraphenylphosphonium tetra-p-tolylborate, tributyl(cyanomethyl)phosphonium chloride, tributyl(1,3-dioxolan-2-ylmethyl)phosphonium bromide, tributyldodecylphosphonium bromide, tributylhexadecylphosphonium bromide, tributylmethylphosphonium iodide, tributyl-n-octylphosphonium bromide, tri-tert-butylphosphonium tetrafluoroborate, tri-tert-butylphosphonium tetraphenylborate, tricyclohexylphosphonium tetrafluoroborate, 2-(trimethylsilyl)ethoxymethyltriphenylphosphonium chloride, (2-trimethylsilylethyl)triphenylphosphonium iodide, (3-trimethylsilyl-2-propyl)triphenylphosphonium bromide, triphenylpropargylphosphonium bromide, triphenylpropylphosphonium bromide, triphenyl(tetradecyl)phosphonium bromide, and triphenylvinylphosphonium bromide.

Further examples include organic phosphine compounds such as trimethylphosphine, triethylphosphine, tributylphosphine and triphenylphosphine, which can give rise to phosphonium cations.

Specific examples of the sulfonium compounds include dimethylsulfoniopropionate, trimethylsulfonyl chloride, trimethylsulfonyl bromide, and trimethylsulfonyl iodide.

Specific examples of the guanidinium compounds include guanidinium chloride, 2-ethyl-1,1,3,3-tetramethylguanidinium chloride, guanidinium bromide, 2-ethyl-1,1,3,3-tetramethylguanidinium bromide, guanidinium hydroxide, and 2-ethyl-1,1,3,3-tetramethylguanidinium hydroxide.

Specific examples of the isouronium compounds include 2-ethyl-1,1,3,3-tetramethylisouronium chloride, 2-ethyl-1,1,3,3-tetramethylisouronium bromide, and 2-ethyl-1,1,3,3-tetramethylisouronium hydroxide.

Specific examples of the isothiouronium compounds include 2-ethyl-1,1,3,3-tetramethylisothiouronium chloride, 2-ethyl-1,1,3,3-tetramethylisothiouronium bromide, and 2-ethyl-1,1,3,3-tetramethylisothiouronium hydroxide.

Among these compounds, onium hydroxide compounds are preferable. By using an onium hydroxide compound, ammonia is produced as a by-product of the reaction, and therefore by removing this ammonia under reduced pressure, the equilibrium can be adjusted to a state that promotes the reaction. By using an onium compound, the inorganic salt by-products can be removed by filtration and water washing, meaning the product can be easily purified.

The amount used of the onium compound is preferably from 0.3 mol to 10 mol, and more preferably from 0.3 mol to 5 mol, relative to 1 mol of the compound [II].

Examples of the organic amine compounds available in the reaction include tertiary amines such as trimethylamine, triethylamine and tributylamine, cyclic amines such as 1,4-diazabicyclo[2.2.2]octane, tertiary amine salts such as trimethylamine hydrochloride, triethylamine hydrochloride, tributylamine hydrochloride, 1,4-diazabicyclo[2.2.2]octane hydrochloride, trimethylamine hydrobromide, triethylamine hydrobromide and tributylamine hydrobromide, and cyclic amine salts such as 1,4-diazabicyclo[2.2.2]octane hydrobromide.

Among these compounds, tertiary amines and cyclic amines are preferable, and tertiary amines are more preferable. By using a tertiary amine or a cyclic amine, ammonia is produced as a by-product in the reaction, and therefore by removing this ammonia under reduced pressure, the equilibrium can be adjusted to a state that promotes the reaction. On the other hand, the inorganic salt by-products that are produced when using a tertiary amine or a cyclic amine can be removed by filtration and water washing, meaning the product can be easily purified.

The amount used of the organic amine compound is preferably from 0.3 mol to 10 mol, and more preferably from 0.3 mol to 5 mol, relative to 1 mol of the compound [II].

There are no particular limitations on the organic solvent available in the reaction. Examples of preferred solvents include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyl oxazolidinone, acetonitrile, valeronitrile, benzonitrile, ethyl acetate, isopropyl acetate, butyl acetate, nitromethane and nitrobenzene. Among these solvents, acetonitrile, ethyl acetate, isopropyl acetate and butyl acetate can be used in both the reaction between the compound [I] and hydrogen fluoride, and the reaction between the compound [III] and at least one compound selected from the group consisting of alkali metal compounds, onium compounds and organic amine compounds, and therefore no solvent substitution is required, and the above reactions can be performed consecutively within the same solvent, which is preferable.

There are no particular limitations on the temperature of the above reaction, but the temperature is preferably from 0° C. to 200° C., and more preferably from 10° C. to 100° C. The time required for the reaction varies depending on the reaction scale, but is preferably from 0.1 hours to 48 hours, and more preferably from 0.5 hours to 24 hours.

Although the reaction can be performed under normal pressure, in those cases where a compound having a hydroxide ion is used, performing the reaction under reduced pressure enables the ammonia that is produced as a by-product to be removed, thereby tilting the equilibrium and facilitating synthesis of the product. When the reaction is performed under reduced pressure, although there are no particular limitations on the reaction pressure, a pressure within a range from atmospheric pressure to 0.01 torr is preferable, and a pressure under which the solvent can be refluxed at a temperature within a range from 0° C. to 100° C. is more preferable.

By performing the above reaction, the compound [IV] can be obtained.

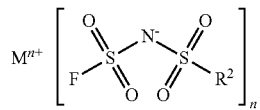

[IV]

In formula [IV], $M^{n+}$ represents an alkali metal cation or an onium cation (excluding $NH_4^+$), n corresponds with the valency of the alkali metal cation or onium cation (excluding $NH_4^+$) and is an integer of 1 to 3, and $R^2$ is the same as defined above in formula [II].

Examples of the alkali metal cation include a lithium cation, sodium cation, potassium cation, rubidium cation and cesium cation. Of these, a lithium cation, sodium cation or potassium cation is preferable.

Examples of the onium cation (excluding $NH_4^+$) include a phosphonium cation, oxonium cation, sulfonium cation, fluoronium cation, chloronium cation, bromonium cation, iodonium cation, selenonium cation, telluronium cation, arsonium cation, stibonium cation, bismutonium cation;

iminium cation, diazenium cation, nitronium cation, diazonium cation, nitrosonium cation, hydrazonium dication, diazenium dication, diazonium dication, imidazolium cation, pyridinium cation, quaternary ammonium cation, tertiary ammonium cation, secondary ammonium cation, primary ammonium cation, piperidinium cation, pyrrolidinium cation, morpholinium cation, pyrazolium cation, guanidinium cation, isouronium cation and isothiouronium cation.

The onium cation is preferably an onium cation having an organic group, namely an organic onium cation. Examples of the organic group include saturated or unsaturated hydrocarbon groups. The saturated or unsaturated hydrocarbon group may be linear, branched or cyclic. The number of carbon atoms that constitute the saturated or unsaturated hydrocarbon group is preferably from 1 to 18, and more preferably from 1 to 8. Examples of atoms or atom groupings that constitute the organic group preferably include a hydrogen atom, fluorine atom, amino group, imino group, amide group, ether group, hydroxyl group, ester group, hydroxyl group, carboxyl group, carbamoyl group, cyano group, sulfone group, sulfide group, nitrogen atom, oxygen atom and sulfur atom; and more preferably include a hydrogen atom, fluorine atom, ether group, hydroxyl group, cyano group and sulfone group. The organic group may have only one of these atoms or atom groupings, or may have at least two of the atoms or atom groupings. When at least two organic groups are bonded, bonds may be formed between the main structures of the organic groups, between the main structures of the organic groups and an aforementioned atom grouping, or between atom groupings described above.

Examples of the onium cation having an organic group include imidazolium cations such as a 1,3-dimethylimidazolium cation, 1-ethyl-3-methylimidazolium cation, 1-propyl-3-methylimidazolium cation, 1-butyl-3-methylimidazolium cation, 1-pentyl-3-methylimidazolium cation, 1-hexyl-3-methylimidazolium cation, 1-heptyl-3-methylimidazolium cation, 1-octyl-3-methylimidazolium cation, 1-decyl-3-methylimidazolium cation, 1-tetradecyl-3-methylimidazolium cation, 1-hexadecyl-3-methylimidazolium cation, 1-octadecyl-3-methylimidazolium cation, 1-allyl-3-ethylimidazolium cation, 1-allyl-3-butylimidazolium cation, 1,3-diallylimidazolium cation, 1-ethyl-2,3-dimethylimidazolium cation, 1-butyl-2,3-dimethylimidazolium cation, 1-hexyl-2,3-methylimidazolium cation, and 1-hexadecyl-2,3-methylimidazolium cation;

pyridinium cations such as a 1-ethylpyridinium cation, 1-butylpyridinium cation, 1-hexylpyridinium cation, 1-octylpyridinium cation, 1-ethyl-3-methylpyridinium cation, 1-ethyl-3-hydroxymethylpyridinium cation, 1-butyl-3-methylpyridinium cation, 1-butyl-4-methylpyridinium cation, 1-octyl-4-methylpyridinium cation, 1-butyl-3,4-dimethylpyridinium cation, and 1-butyl-3,5-dimethylpyridinium cation;

quaternary ammonium cations such as a tetramethylammonium cation, tetraethylammonium cation, tetrapropylammonium cation, tetrabutylammonium cation, tetraheptylammonium cation, tetrahexylammonium cation, tetraoctylammonium cation, triethylmethylammonium cation, propyltrimethylammonium cation, diethyl-2-methoxyethylmethylammonium cation, methyltrioctylammonium cation, cyclohexyltrimethylammonium cation, 2-hydroxyethyltrimethylammonium cation, trimethylphenylammonium cation, benzyltrimethylammonium cation, benzyltributylammonium cation, benzyltriethylammonium cation, dimethyldistearylammonium cation, diallyldimethylammonium cation, 2-methoxyethoxymethyltrimethylammonium cation, and tetrakis(pentafluoroethyl)ammonium cation;

tertiary ammonium cations such as a trimethylammonium cation, triethylammonium cation, tributylammonium cation, diethylmethylammonium cation, dimethylethylammonium cation, dibutylmethylammonium cation, and 4-aza-1-azoniabicyclo[2.2.2]octane cation; secondary ammonium cations such as a dimethylammonium cation, diethylammonium cation, and dibutylammonium cation; primary ammonium cations such as a methylammonium cation, ethylammonium cation, butylammonium cation, hexylammonium cation, and octylammonium cation; organic ammonium cations such as an N-methoxytrimethylammonium cation, N-ethoxytrimethylammonium cation, and N-propoxytrimethylammonium cation; piperidinium cations such as a 1-propyl-1-methylpiperidinium cation and 1-(2-methoxyethyl)-1-methylpiperidinium cation; pyrrolidinium cations such as a 1-propyl-1-methylpyrrolidinium cation, 1-butyl-1-methylpyrrolidinium cation, 1-hexyl-1-methylpyrrolidinium cation, and 1-octyl-1-methylpyrrolidinium cation; morpholinium cations such as a 4-propyl-4-methylmorpholinium cation and 4-(2-methoxyethyl)-4-methylmorpholinium cation; pyrazolium cations such as a 2-ethyl-1,3,5-trimethylpyrazolium cation, 2-propyl-1,3,5-trimethylpyrazolium cation, 2-butyl-1,3,5-trimethylpyrazolium cation, and 2-hexyl-1,3,5-trimethylpyrazolium cation;

guanidinium cations such as a 2-ethyl-1,1,3,3-tetramethylguanidinium cation; sulfonium cations such as a trimethylsulfonium cation; phosphonium cations such as a trihexyltetradecylphosphonium cation; isouronium cations such as a 2-ethyl-1,1,3,3-tetramethylisouronium cation; and isothiouronium cations such as a 2-ethyl-1,1,3,3-tetramethylisothiouronium cation.

Among these, imidazolium cations such as a 1,3-dimethylimidazolium cation, 1-ethyl-3-methylimidazolium cation, 1-butyl-3-methylimidazolium cation, 1-hexyl-3-methylimidazolium cation, 1-octyl-3-methylimidazolium cation, 1-allyl-3-ethylimidazolium cation, 1-allyl-3-butylimidazolium cation, 1,3-diallylimidazolium cation, 1-ethyl-2,3-dimethylimidazolium cation, 1-butyl-2,3-dimethylimidazolium cation, and 1-hexyl-2,3-dimethylimidazolium cation; and organic ammonium cations such as a propyltrimethylammonium cation, diethyl-2-methoxyethylmethylammonium cation, methyltrioctylammonium cation, cyclohexyltrimethylammonium cation, 2-hydroxyethyltrimethylammonium cation, trimethylammonium cation, triethylammonium cation, tributylammonium cation, and 4-aza-1-azoniabicyclo [2.2.2]octane cation are preferable. Among these, cations that contain no metal elements that degrade electrolyte properties and the like, such as tertiary ammonium cations, specifically, a trimethylammonium cation, triethylammonium cation and tributylammonium cation are more preferable as the onium cation.

Specific examples of the compound [IV] include lithium di(fluorosulfonyl)imide, lithium N-(fluorosulfonyl)-N-(trifluoromethylsulfonyl)imide, lithium N-(fluorosulfonyl)-N-(pentafluoroethylsulfonyl)imide, and lithium N-(fluorosulfonyl)-N-(perfluoro-n-propylsulfonyl)imide; potassium di(fluorosulfonyl)imide, potassium N-(fluorosulfonyl)-N-(trifluoromethylsulfonyl)imide, potassium N-(fluorosulfonyl)-N-(pentafluoroethylsulfonyl)imide, and potassium N-(fluorosulfonyl)-N-(perfluoro-n-propylsulfonyl)imide; sodium di(fluorosulfonyl)imide, sodium N-(fluorosulfonyl)-N-(trifluoromethylsulfonyl)imide, sodium N-(fluorosulfonyl)-N-(pentafluoroethylsulfonyl)imide, and sodium N-(fluorosulfonyl)-N-(perfluoro-n-propylsulfonyl)imide;

1,3-dimethylimidazolium di(fluorosulfonyl)imide, 1,3-dimethylimidazolium N-(fluorosulfonyl)-N-(trifluoromethylsulfonyl)imide, 1,3-dimethylimidazolium N-(fluorosulfonyl)-N-(pentafluoroethylsulfonyl)imide, and 1,3-dimethylimidazolium N-(fluorosulfonyl)-N-(perfluoro-n-propylsulfonyl)imide; 1-ethyl-3-methylimidazolium di(fluorosulfonyl)imide, 1-ethyl-3-methylimidazolium N-(fluorosulfonyl)-N-(trifluoromethylsulfonyl)imide, 1-ethyl-3-methylimidazolium N-(fluorosulfonyl)-N-(pentafluoroethylsulfonyl)imide, and 1-ethyl-3-methylimidazolium N-(fluorosulfonyl)-N-(perfluoro-n-propylsulfonyl)imide; 1-butyl-3-methylimidazolium di(fluorosulfonyl)imide, 1-butyl-3-methylimidazolium N-(fluorosulfonyl)-N-(trifluoromethylsulfonyl)imide, 1-butyl-3-methylimidazolium N-(fluorosulfonyl)-N-(pentafluoroethylsulfonyl)imide, and 1-butyl-3-methylimidazolium N-(fluorosulfonyl)-N-(perfluoro-n-propylsulfonyl)imide; 1-hexyl-3-methylimidazolium di(fluorosulfonyl)imide, 1-hexyl-3-methylimidazolium N-(fluorosulfonyl)-N-(trifluoromethylsulfonyl)imide, 1-hexyl-3-methylimidazolium N-(fluorosulfonyl)-N-(pentafluoroethylsulfonyl)imide, and 1-hexyl-3-methylimidazolium N-(fluorosulfonyl)-N-(perfluoro-n-propylsulfonyl)imide;

1-octyl-3-methylimidazolium di(fluorosulfonyl)imide, 1-octyl-3-methylimidazolium N-(fluorosulfonyl)-N-(trifluoromethylsulfonyl)imide, 1-octyl-3-methylimidazolium N-(fluorosulfonyl)-N-(pentafluoroethylsulfonyl)imide, and 1-octyl-3-methylimidazolium N-(fluorosulfonyl)-N-(perfluoro-n-propylsulfonyl)imide; 1-allyl-3-ethylimidazolium di(fluorosulfonyl)imide, 1-allyl-3-ethylimidazolium N-(fluorosulfonyl)-N-(trifluoromethylsulfonyl)imide, 1-allyl-3-ethylimidazolium N-(fluorosulfonyl)-N-(pentafluoroethylsulfonyl)imide, and 1-allyl-3-ethylimidazolium N-(fluorosulfonyl)-N-(perfluoro-n-propylsulfonyl)imide; 1-allyl-3-butylimidazolium di(fluorosulfonyl)imide, 1-allyl-3-butylimidazolium N-(fluorosulfonyl)-N-(trifluoromethylsulfonyl)imide, 1-allyl-3-butylimidazolium N-(fluorosulfonyl)-N-(pentafluoroethylsulfonyl)imide, and 1-allyl-3-butylimidazolium N-(fluorosulfonyl)-N-(perfluoro-n-propylsulfonyl)imide; 1,3-diallylimidazolium di(fluorosulfonyl)imide, 1,3-diallylimidazolium N-(fluorosulfonyl)-N-(trifluoromethylsulfonyl)imide, 1,3-diallylimidazolium N-(fluorosulfonyl)-N-(pentalluoroethylsulfonyl)imide, and 1,3-diallylimidazolium N-(fluorosulfonyl)-N-(perfluoro-n-propylsulfonyl)imide; 1-ethyl-2,3-dimethylimidazolium di(fluorosulfonyl)imide, 1-ethyl-2,3-dimethylimidazolium N-(fluorosulfonyl)-N-(trifluoromethylsulfonyl)imide, 1-ethyl-2,3-dimethylimidazolium N-(fluorosulfonyl)-N-(pentalluoroethylsulfonyl)imide, and 1-ethyl-2,3-dimethylimidazolium N-(fluorosulfonyl)-N-(perfluoro-n-propylsulfonyl)imide;

1-butyl-2,3-dimethylimidazolium di(fluorosulfonyl)imide, 1-butyl-2,3-dimethylimidazolium N-(fluorosulfonyl)-N-(trifluoromethylsulfonyl)imide, 1-butyl-2,3-dimethylimidazolium N-(fluorosulfonyl)-N-(pentafluoroethylsulfonyl)imide, and 1-butyl-2,3-dimethylimidazolium N-(fluorosulfonyl)-N-(perfluoro-n-propylsulfonyl)imide; 1-hexyl-2,3-dimethylimidazolium di(fluorosulfonyl)imide, 1-hexyl-2,3-dimethylimidazolium N-(fluorosulfonyl)-N-(trifluoromethylsulfonyl)imide, 1-hexyl-2,3-dimethylimidazolium N-(fluorosulfonyl)-N-(pentafluoroethylsulfonyl)imide, and 1-hexyl-2,3-dimethylimidazolium N-(fluorosulfonyl)-N-(perfluoro-n-propylsulfonyl)imide;

1-butylpyridinium di(fluorosulfonyl)imide, 1-butylpyridinium N-(fluorosulfonyl)-N-(trifluoromethylsulfonyl)imide, 1-butylpyridinium N-(fluorosulfonyl)-N-(pentafluoroethylsulfonyl)imide, and 1-butylpyridinium N-(fluorosulfonyl)-N-(perfluoro-n-propylsulfonyl)imide; 1-hexylpyridinium di(fluorosulfonyl)imide, 1-hexylpyridinium N-(fluorosulfonyl)-N-(trifluoromethylsulfonyl)imide, 1-hexylpyridinium N-(fluorosulfonyl)-N-(pentafluoroethylsulfonyl)imide, and 1-hexylpyridinium N-(fluorosulfonyl)-N-(perfluoro-n-propylsulfonyl)imide; 1-octylpyridinium di(fluorosulfonyl)imide, 1-octylpyridinium N-(fluorosulfonyl)-N-(trifluoromethylsulfonyl)imide, 1-octylpyridinium N-(fluorosulfonyl)-N-(pentafluoroethylsulfonyl)imide, and 1-octylpyridinium N-(fluorosulfonyl)-N-(perfluoro-n-propylsulfonyl)imide; 1-ethyl-3-methylpyridinium di(fluorosulfonyl)imide, 1-ethyl-3-methylpyridinium N-(fluorosulfonyl)-N-(trifluoromethylsulfonyl)imide, 1-ethyl-3-methylpyridinium N-(fluorosulfonyl)-N-(pentafluoroethylsulfonyl)imide, and 1-ethyl-3-methylpyridinium N-(fluorosulfonyl)-N-(perfluoro-n-propylsulfonyl)imide;

1-butyl-3-methylpyridinium di(fluorosulfonyl)imide, 1-butyl-3-methylpyridinium N-(fluorosulfonyl)-N-(trifluoromethylsulfonyl)imide, 1-butyl-3-methylpyridinium N-(fluorosulfonyl)-N-(pentafluoroethylsulfonyl)imide, and 1-butyl-3-methylpyridinium N-(fluorosulfonyl)-N-(perfluoro-n-propylsulfonyl)imide; 1-butyl-4-methylpyridinium di(fluorosulfonyl)imide, 1-butyl-4-methylpyridinium N-(fluorosulfonyl)-N-(trifluoromethylsulfonyl)imide, 1-butyl-4-methylpyridinium N-(fluorosulfonyl)-N-(pentafluoroethylsulfonyl)imide, and 1-butyl-4-methylpyridinium N-(fluorosulfonyl)-N-(perfluoro-n-propylsulfonyl)imide;

diethyl-2-methoxyethylmethylammonium di(fluorosulfonyl)imide, diethyl-2-methoxyethylmethylammonium N-(fluorosulfonyl)-N-(trifluoromethylsulfonyl)imide, diethyl-2-methoxyethylmethylammonium N-(fluorosulfonyl)-N-(pentafluoroethylsulfonyl)imide, and diethyl-2-methoxyethylmethylammonium N-(fluorosulfonyl)-N-(perfluoro-n-propylsulfonyl)imide; methyltrioctylammonium di(fluorosulfonyl)imide, methyltrioctylammonium N-(fluorosulfonyl)-N-(trifluoromethylsulfonyl)imide, methyltrioctylammonium N-(fluorosulfonyl)-N-(pentafluoroethylsulfonyl)imide, and methyltrioctylammonium N-(fluorosulfonyl)-N-(perfluoro-n-propylsulfonyl)imide; cyclohexyltrimethylammonium di(fluorosulfonyl)imide, cyclohexyltrimethylammonium N-(fluorosulfonyl)-N-(trifluoromethylsulfonyl)imide, cyclohexyltrimethylammonium N-(fluorosulfonyl)-N-(pentalluoroethylsulfonyl)imide, and cyclohexyltrimethylammonium N-(fluorosulfonyl)-N-(perfluoro-n-propylsulfonyl)imide;

trimethylammonium di(fluorosulfonyl)imide, trimethylammonium N-(fluorosulfonyl)-N-(trifluoromethylsulfonyl)imide, trimethylammonium N-(fluorosulfonyl)-N-(pentafluoroethylsulfonyl)imide, and trimethylammonium N-(fluorosulfonyl)-N-(perfluoro-n-propylsulfonyl)imide; triethylammonium di(fluorosulfonyl)imide, triethylammonium N-(fluorosulfonyl)-N-(trifluoromethylsulfonyl)imide, triethylammonium N-(fluorosulfonyl)-N-(pentafluoroethylsulfonyl)imide, and triethylammonium N-(fluorosulfonyl)-N-(perfluoro-n-propylsulfonyl)imide; tributylammonium di(fluorosulfonyl)imide, tributylammonium N-(fluorosulfonyl)-N-(trifluoromethylsulfonyl)imide, tributylammonium N-(fluorosulfonyl)-N-(pentafluoroethylsulfonyl)imide, and tributylammonium N-(fluorosulfonyl)-N-(perfluoro-n-propylsulfonyl)imide; 4-aza-1-azoniabicyclo[2.2.2]octane di(fluorosulfonyl)imide, 4-aza-1-azoniabicyclo[2.2.2]octane N-(fluorosulfonyl)-N-(trifluoromethylsulfonyl)imide, 4-aza-1-azoniabicyclo[2.2.2]octane N-(fluorosulfonyl)-N-(pentafluoroethylsulfonyl)imide, and 4-aza-1-azoniabicyclo[2.2.2]octane N-(fluorosulfonyl)-N-(perfluoro-n-propylsulfonyl)imide;

1-propyl-1-methylpiperidinium di(fluorosulfonyl)imide, 1-propyl-1-methylpiperidinium N-(fluorosulfonyl)-N-(trifluoromethylsulfonyl)imide, 1-propyl-1-methylpiperidinium N-(fluorosulfonyl)-N-(pentafluoroethylsulfonyl)imide, and 1-propyl-1-methylpiperidinium N-(fluorosulfonyl)-N-(perfluoro-n-propylsulfonyl)imide; 1-propyl-1-methylpyrrolidinium di(fluorosulfonyl)imide, 1-propyl-1-methylpyrrolidinium N-(fluorosulfonyl)-N-(trifluoromethylsulfonyl)imide, 1-propyl-1-methylpyrrolidinium N-(fluorosulfonyl)-N-(pentafluoroethylsulfonyl)imide, and 1-propyl-1-methylpyrrolidinium N-(fluorosulfonyl)-N-(perfluoro-n-propylsulfonyl)imide; 1-butyl-1-methylpyrrolidinium di(fluorosulfonyl)imide, 1-butyl-1-methylpyrrolidinium N-(fluorosulfonyl)-N-(trifluoromethylsulfonyl)imide, 1-butyl-1-methylpyrrolidinium N-(fluorosulfonyl)-N-(pentafluoroethylsulfonyl)imide, and 1-butyl-1-methylpyrrolidinium N-(fluorosulfonyl)-N-(perfluoro-n-propylsulfonyl)imide;

4-propyl-4-methylmorpholinium di(fluorosulfonyl)imide, 4-propyl-4-methylmorpholinium N-(fluorosulfonyl)-N-(trifluoromethylsulfonyl)imide, 4-propyl-4-methylmorpholinium N-(fluorosulfonyl)-N-(pentafluoroethylsulfonyl)imide, and 4-propyl-4-methylmorpholinium N-(fluorosulfonyl)-N-(perfluoro-n-propylsulfonyl)imide; 2-butyl-1,3,5-trimethylpyrazolium di(fluorosulfonyl)imide, 2-butyl-1,3,5-trimethylpyrazolium N-(fluorosulfonyl)-N-(trifluoromethylsulfonyl)imide, 2-butyl-1,3,5-trimethylpyrazolium N-(fluorosulfonyl)-N-(pentafluoroethylsulfonyl)imide, and 2-butyl-1,3,5-trimethylpyrazolium N-(fluorosulfonyl)-N-(perfluoro-n-propylsulfonyl)imide;

2-ethyl-1,1,3,3-tetramethylguanidinium di(fluorosulfonyl)imide, 2-ethyl-1,1,3,3-tetramethylguanidinium N-(fluorosulfonyl)-N-(trifluoromethylsulfonyl)imide, 2-ethyl-1,1,3,3-tetramethylguanidinium N-(fluorosulfonyl)-N-(pentafluoroethylsulfonyl)imide, and 2-ethyl-1,1,3,3-tetramethylguanidinium N-(fluorosulfonyl)-N-(perfluoro-n-propylsulfonyl)imide; trimethylsulfonium di(fluorosulfonyl)imide, trimethylsulfonium N-(fluorosulfonyl)-N-(trifluoromethylsulfonyl)imide, trimethylsulfonium N-(fluorosulfonyl)-N-(pentafluoroethylsulfonyl)imide, and trimethylsulfonium N-(fluorosulfonyl)-N-(perfluoro-n-propylsulfonyl)imide; trihexyltetradecylphosphonium di(fluorosulfonyl)imide, trihexyltetradecylphosphonium N-(fluorosulfonyl)-N-(trifluoromethylsulfonyl)imide, trihexyltetradecylphosphonium N-(fluorosulfonyl)-N-(pentafluoroethylsulfonyl)imide, and trihexyltetradecylphosphonium N-(fluorosulfonyl)-N-(perfluoro-n-propylsulfonyl)imide;

2-ethyl-1,1,3,3-tetramethylisouronium di(fluorosulfonyl)imide, 2-ethyl-1,1,3,3-tetramethylisouronium N-(fluorosulfonyl)-N-(trifluoromethylsulfonyl)imide, 2-ethyl-1,1,3,3-tetramethylisouronium N-(fluorosulfonyl)-N-(pentafluoroethylsulfonyl)imide, and 2-ethyl-1,1,3,3-tetramethylisouronium N-(fluorosulfonyl)-N-(perfluoro-n-propylsulfonyl)imide; 2-ethyl-1,1,3,3-tetramethylisothiouronium di(fluorosulfonyl)imide, 2-ethyl-1,1,3,3-tetramethylisothiouronium N-(fluorosulfonyl)-N-(trifluoromethylsulfonyl)imide, 2-ethyl-1,1,3,3-tetramethylisothiouronium N-(fluorosulfonyl)-N-(pentafluoroethylsulfonyl)imide, and 2-ethyl-1,1,3,3-tetramethylisothiouronium N-(fluorosulfonyl)-N-(perfluoro-n-propylsulfonyl)imide.

The compound [IV] obtained in accordance with the production process of the present invention contains a smaller amount of contamination by metal impurities that degrade the electrolyte properties and the like when compared with compounds obtained by conventional processes, and can therefore be used favorably as a material for an ion conductor used in forming primary cells, secondary cells such as a lithium ion secondary cell, and electrochemical devices such as electrolytic capacitors, electrical double-layer capacitors, fuel cells, solar cells and electrochromic elements.

EXAMPLES

The present invention is described below in further detail based on a series of examples. However, the present invention is in no way limited by the following examples, and appropriate changes can, of course, be made while still conforming with the purport of the present invention, and such changes are all deemed to be included within the technical scope of the present invention.

Synthesis Example 1

A 500 ml reaction vessel equipped with a stirrer, a thermometer and a reflux condenser was charged with 123.9 g (1.10 mol) of chlorosulfonic acid ($ClSO_3H$) and 98.1 g (0.70 mol) of chlorosulfonyl isocyanate. The temperature of this mixed liquid was raised to 130° C. under stirring over a period of 2.5 hours, and reaction was performed at this temperature for 9 hours. Following completion of the reaction, a reduced pressure distillation was performed, and a fraction was collected at 98.5° C. to 101° C./4.2 torr. Di(chlorosulfonyl)imide was obtained as a colorless transparent liquid in an amount of 77.9 g (0.36 mol).

Example 1

Synthesis of ammonium di(chlorosulfonyl)imide

A reaction vessel was charged with 21.4 g (100 mmol) of the di(chlorosulfonyl)imide obtained in Synthesis Example 1. Then, 100 ml of acetonitrile and 5.4 g (100 mmol) of ammonium chloride were added to the vessel, and a reaction was performed at 23 to 26° C. for 1.5 hours under constant stirring. Following completion of the reaction, the solid was removed by filtration and washed with acetonitrile. The solvent was removed from the obtained organic phase by distillation under reduced pressure, and 25.4 g of a yellow oily substance was obtained.

Synthesis of ammonium di(fluorosulfonyl)imide

A reaction vessel was charged, at −20° C., with 5.2 ml (240 mmol) of anhydrous hydrogen fluoride and 30 ml of acetonitrile. To this was added, over a period of 6 minutes, a 30 ml acetonitrile solution of 15.3 g of the ammonium di(chlorosulfonyl)imide synthesized above. Following completion of the addition, the temperature was raised to 80° C. over a period of 1.5 hours, and a reaction was then performed under reflux at 80 to 84° C. for 2.5 hours. Following completion of the reaction, the temperature was cooled to room temperature, and the hydrogen fluoride was flushed out by nitrogen bubbling. Ethyl acetate and water were then added to the vessel, and a neutralization was then performed with ammonium hydrogen carbonate. The solid was removed by filtration. Subsequently, the organic phase was separated. The water phase was extracted 3 times with ethyl acetate. The organic phases obtained in the extraction operations were combined, and the combined organic phase was washed with water. The solvent was then removed by distillation under reduced pressure. The thus obtained substance was analyzed by $^{19}$F-NMR. The areas of the peaks in the analysis chart were measured, and the substitution rate from chlorine to fluorine was quantified. Ammonium di(fluorosulfonyl)imide was obtained in an amount of 10.5 g (53.4 mmol).

Example 2

Synthesis of potassium di(fluorosulfonyl)imide

A reaction vessel was charged with 6.2 g (23.5 mmol) of ammonium di(fluorosulfonyl)imide, 47 ml of butyl acetate, and a 20% aqueous solution containing 16.5 g (58.8 mmol) of potassium hydroxide, and the mixture was refluxed under reduced pressure at 65 torr and at 37° C. for one hour. The reaction liquid was then cooled to 25° C. Subsequently, a liquid-liquid separation was performed, and the water phase was extracted 3 times with 24 ml of butyl acetate. The organic phases obtained in the extraction operations were combined, and the solvent was then removed from the organic phase by distillation under reduced pressure. Then, 39 ml of methylene chloride was added, and the mixture was stirred at room temperature for 30 minutes. Subsequently, the crystals were collected by filtration. The thus obtained crystals were washed with 39 ml of methylene chloride, and were then dried at room temperature under reduced pressure. Potassium di(fluorosulfonyl)imide was obtained in an amount of 4.6 g. The results of quantitative analysis by cation chromatography revealed that the entire product was composed of the potassium salt, and contained no ammonium ions.

Example 3

Synthesis of lithium di(fluorosulfonyl)imide

To 9.8 g (49.6 mmol) of ammonium di(fluorosulfonyl)imide were added 99 ml of butyl acetate, 6.2 g (148.8 mmol) of lithium hydroxide monohydrate and 37 ml of water, and the mixture was refluxed under reduced pressure at 65 torr and at 37° C. for one hour. The reaction liquid was then cooled to 25° C. Subsequently, a liquid-liquid separation was performed, and the water phase was extracted 3 times with 50 ml of butyl acetate. The organic phases obtained in the extraction operations were combined, and then washed twice with 3 ml of water. Subsequently, the solvent was removed by distillation under reduced pressure. Then, 50 ml of methylene chloride was added, and the mixture was stirred at room temperature for 19 hours. Subsequently, the crystals were collected by filtration. The thus obtained crystals were washed with 50 ml of methylene chloride, and were then dried at room temperature under reduced pressure. Lithium di(fluorosulfonyl)imide was obtained in an amount of 4.5 g. The results of quantitative analysis by cation chromatography revealed that the entire product was composed of the lithium salt, and contained no ammonium ions.

Example 4

Synthesis of sodium di(fluorosulfonyl)imide

To 4.9 g (24.7 mmol) of ammonium di(fluorosulfonyl) imide were added 49 ml of butyl acetate and a 20% aqueous solution containing 12.4 g (61.8 mmol) of sodium hydroxide, and the mixture was refluxed under reduced pressure at 65 torr and at 37° C. for one hour. The reaction liquid was then cooled to 25° C. Subsequently, a liquid-liquid separation was performed, and the water phase was extracted 3 times with 25 ml of butyl acetate. The organic phases obtained in the extraction operations were combined, and the solvent was then removed from the organic phase by distillation under reduced pressure. Then, 41 ml of methylene chloride was added, and the mixture was stirred at room temperature for 15 minutes. Subsequently, the crystals were collected by filtration. The thus obtained crystals were washed with 20 ml of methylene chloride, and were then dried at room temperature under reduced pressure. Sodium di(fluorosulfonyl)imide was obtained in an amount of 3.5 g. The results of quantitative analysis by cation chromatography revealed that the entire product was composed of the sodium salt, and contained no ammonium ions.

Example 5

Synthesis of triethylammonium di(fluorosulfonyl)imide

To a separating funnel were added 0.88 g (4.46 mmol) of ammonium di(fluorosulfonyl)imide, 10 ml of butyl acetate, 1.38 g (10.00 mmol) of triethylamine hydrochloride and 1 ml of water, and the components were mixed thoroughly. Subsequently, a liquid-liquid separation was performed, and the organic phase was washed 4 times with 1 ml of water. The solvent was then removed by distillation under reduced pressure, yielding 1.02 g of triethylammonium di(fluorosulfonyl) imide. The results of $^1$H-NMR measurements confirmed that the triethylammonium salt had been produced.

INDUSTRIAL APPLICABILITY

According to the present invention, fluorosulfonylimide ammonium salts can be produced in an industrially efficient manner. Further, by reacting the thus obtained fluorosulfonylimide ammonium salt with an alkali metal compound or the like, another fluorosulfonylimide salt containing no metal impurities that degrade electrolyte properties and the like can be produced.

The invention claimed is:
1. A process for producing a fluorosulfonylimide ammonium salt of formula II, the process comprising reacting a compound of formula I and hydrogen fluoride:

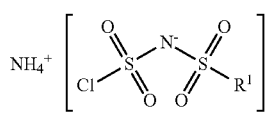

wherein $R^1$ represents a fluorine atom, a chlorine atom, or a fluoroalkyl group having 1 to 6 carbon atoms,

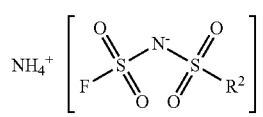

wherein R² represents a fluorine atom or a fluoroalkyl group having 1 to 6 carbon atoms.

2. The process according to claim 1, further comprising reacting a compound of formula III with ammonia or a slat thereof to obtain the compound of formula I:

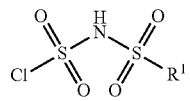
III wherein R¹ is as defined in formula I.

3. A process for producing a fluorosulfonylimide salt of formula IV, the process comprising reacting a fluorosulfonylimide ammonium salt of formula II obtained by a process according to claim 1 with at least one compound selected from the group consisting of alkali metal compounds, onium compounds and organic amine compounds:

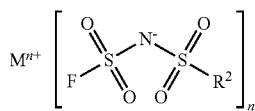
IV wherein $M^{n+}$ represents an alkali metal cation or an onium cation (excluding $NH_4^+$), n corresponds with a valency of the alkali metal cation or onium cation (excluding $NH_4^+$) and is an integer of 1 to 3, and R² is as defined in formula II.

4. The process disclosed according to claim 3, wherein the fluorosulfonylimide ammonium salt of formula II is reacted with an alkali metal hydroxide or a tertiary amine compound, and $M^{n+}$ in formula IV represents an alkali metal cation or a tertiary ammonium cation.

* * * * *